United States Patent [19]
Chen et al.

[11] 4,311,865
[45] Jan. 19, 1982

[54] MANUFACTURE OF HYDROCARBONS FROM OXYGENATES

[75] Inventors: Nai-Yuen Chen, Titusville; Joseph N. Miale, Lawrenceville; William J. Reagan, Englishtown, all of N.J.

[73] Assignee: Mobil Oil Corporation, New York, N.Y.

[21] Appl. No.: 122,638

[22] Filed: Feb. 19, 1980

Related U.S. Application Data

[62] Division of Ser. No. 27,186, Apr. 4, 1979, abandoned.

[51] Int. Cl.$^3$ ............................................. C07C 1/00
[52] U.S. Cl. ..................................... 585/640; 585/408
[58] Field of Search ....................... 585/408, 639, 640

[56] References Cited

U.S. PATENT DOCUMENTS 3,804,746  4/1974  Chu .................................. 252/455 Z
3,992,466  11/1976  Plank et al. ..................... 252/455 Z
4,076,761  2/1978  Chang et al. ......................... 585/640
4,100,262  7/1978  Pelrine ............................. 252/455 Z Primary Examiner—Curtis R. Davis
Attorney, Agent, or Firm—C. A. Huggett; C. J. Speciale; V. J. Frilette

[57] ABSTRACT

This invention provides a novel catalyst exemplified by cobalt-exchanged ZSM-5. The catalyst has unusual resistance to irreversible steam degradation. After long-term exposure to steam, it may be regenerated by sulfiding. The invention further provides a process for converting, in the presence of steam, compounds subject to catalytic conversion by acidic catalysts, including a process in which steam is inherently produced. The latter conversion is exemplified by the formation of higher carbon-numbered hydrocarbons from the lower alcohols or ethers thereof.

8 Claims, 1 Drawing Figure

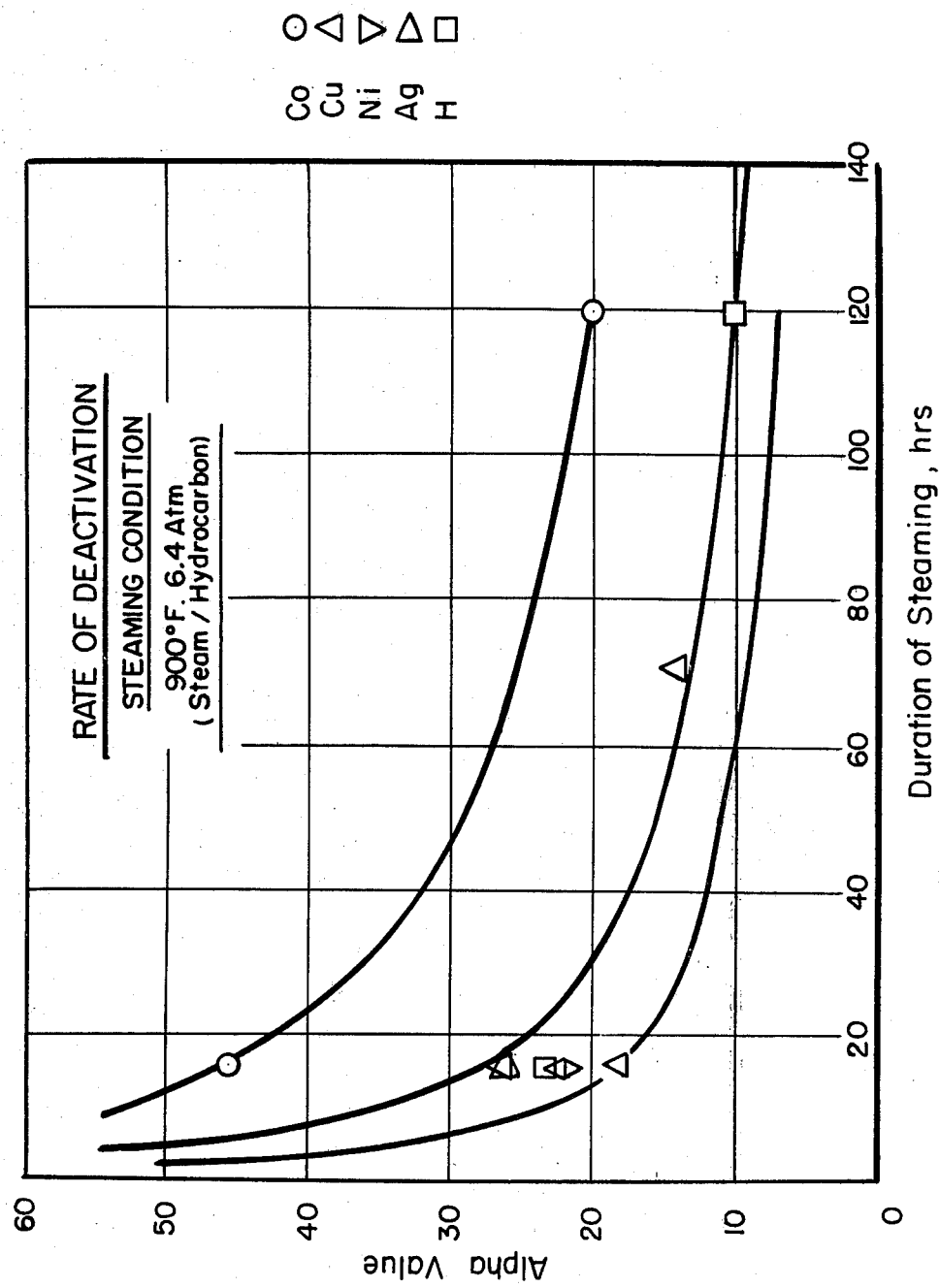

MANUFACTURE OF HYDROCARBONS FROM OXYGENATES

This is a division of copending application Ser. No. 27,186, filed Apr. 4, 1979, and now abandoned.

BACKGROUND OF THE INVENTION

1. Field of the Invention

This invention is concerned with an improved process for catalytic conversion of a hydrocarbon or an oxygenated compound feed, during which process the catalyst is exposed to steam and hydrocarbons. It is particularly concerned with the catalytic conversion of lower alcohols and ethers to hydrocarbons and steam utilizing, as stabilized catalyst, cobalt-impregnated ZSM-5, for example.

2. Description of the Prior Art

A remarkable growth in the production of synthetic fibers, plastics and rubber has taken place in recent decades. This growth, to a very large extent, has been supported and encouraged by an expanding supply of inexpensive petrochemical raw materials such as ethylene, benzene, toluene, and xylenes. Side by side with this remarkable development, there has been an increasing demand for aromatic hydrocarbons for use as high octane gasoline components. Environmental factors which limit the lead content of gasoline are likely to aggravate the need for aromatics.

Burgeoning demand for olefins, particularly ethylene, and for aromatic hydrocarbons, has of course led to periods of shortage, either due to short supply of suitable feedstocks or to limited processing capacity. In any case, it would appear desirable to provide sufficient means for converting raw materials other than petroleum to olefins and aromatic hydrocarbons.

U.S. Pat. Nos. 3,894,106, 3,894,107 and 3,907,915, respectively, disclose the conversion of alcohols, ethers, carbonyls, or mixtures thereof to higher carbon number hydrocarbons by contact with a catalyst comprising a crystalline aluminosilicate zeolite having a silica to alumina ratio of at least about 12 and a Constraint Index of about 1 to 12.

The conversion of methanol and dimethyl ether to hydrocarbon is described in U.S. Pat. No. 3,911,041.

All of the foregoing patents are herein incorporated by reference for background, and they illustrate recently developed art for efficiently converting oxygenated compounds to hydrocarbons and steam. In each of these patents a novel type of catalyst, exemplified by ZSM-5, is used. This novel type is characterized by unusual thermal stability and resistance to degradation by steam. Nonetheless, with protracted use of such catalyst for reactions which inherently form steam, loss of catalytic activity does occur which is not recoverable by burning in air or by other recognized techniques for regeneration.

Catalytic conversion of hydrocarbons in the presence of hydrogen sulfide or of sulfur compounds is described in U.S. Pat. Nos. 3,173,855 issued Mar. 16, 1965 and 3,175,967 issued Mar. 30, 1965 to Miale et al.

It is an object of this invention to provide a novel long-lived catalyst resistant to irreversible deactivation by steam. It is a further object of this invention to provide a catalytic process for the conversion of oxygenated compounds to hydrocarbons and steam with provision for regenerating the catalyst. It is a further object of this invention to provide a process for the conversion of alcohols, ethers, carbonyl compounds, or mixtures thereof, to higher carbon number hydrocarbons by contact with a catalyst comprising a crystalline zeolite having a $SiO_2/Al_2O_3$ ratio of at least about 12 and a Constraint Index of about 1 to 12 with minimal irreversible loss of catalytic activity. It is a further object of this invention to provide a process for converting oxygenated compounds to hydrocarbons and steam by catalytic contact with a regenerable cobalt-exchanged zeolite catalyst. These as well as other objects will become apparent on reading this entire specification including the claims.

SUMMARY OF THE INVENTION

It has been found that cobalt composited with a crystalline zeolite having a $SiO_2/Al_2O_3$ ratio of at least 12 and a Constraint Index of 1 to 12 is a catalytic composition unusually resistant to irreversible deterioration when exposed at high temperature to steam and hydrocarbons. When deterioration does occur, the catalyst may be regenerated by contact with hydrogen sulfide. The foregoing composition is further characterized by a low sodium content and a minimum catalyst activity defined by an "alpha value" of at least 10, as more fully described hereinbelow.

The process of this invention utilizes the above-described cobalt-impregnated or exchanged crystalline zeolite composition as catalyst. In this process, a substantially sulfur-free feed comprising an oxygenated compound is contacted with the catalyst under conversion conditions, thereby converting the oxygenated compound to hydrocarbon and steam. After a protracted period of time, the catalyst, which becomes deactivated due to the high temperature exposure to steam, is contacted with hydrogen sulfide, restoring its catalytic activity, and the conversion of the oxygenated compound is resumed. This restoration of catalytic activity may be practiced one or more times, or until the hydrogen sulfide treatment is no longer effective in restoring catalytic activity.

The foregoing catalyst and process are particularly adapted to the conversion of the lower alcohols or their corresponding ethers to higher carbon numbered hydrocarbons, i.e. to conversions which inherently produce steam. However, as will be recognized by one skilled in the art, the process of the present invention also offers advantages for any acid-catalyzed conversion of a convertible organic compound in the presence of steam, and such variant of the process is contemplated as within the scope of this invention.

DETAILED DESCRIPTION OF THE INVENTION

The novel catalyst of this invention is prepared by compositing cobalt with a particular crystalline zeolite. Compositing may be effected by ion-exchange of the zeolite with a cobalt salt, by impregnation of the zeolite with a soluble cobalt compound, and by other means which lead to an intimate association of the cobalt with the zeolite. Regardless of the method of compositing, the catalyst composition of this invention is required to be substantially free of sodium, i.e. to have a sodium content less than about 0.5 wt. % computed as $Na_2O$. This is readily achieved, for example, by compositing the cobalt with the hydrogen form or the ammonium form of the zeolite, and by other methods known to those skilled in the art. Regardless of the method of compositing, the catalyst also is required to have a CoO/Al$_2$O$_3$ (i.e. a cobalt oxide to zeolitic alumina molar ratio) of 0.1 to about 1.0.

The particular crystalline zeolite utilized herein may be any member of the novel class of zeolites now to be described. Although these zeolites have unusually low alumina contents, i.e. high silica to alumina ratios, they are very active even when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. 12-membered rings usually do not offer sufficient constraint to produce the advantageous conversions, although the puckered 12-ring structure of TMA offretite shows constrained access. Other 12-ring structures may exist which, due to pore blockage or to other cause, may be operative.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of normal hexane and 3-methylpentane over a small sample, approximately one gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature is adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of n-hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| CAS | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indexes. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-23, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosolicates are ZSM-5, ZSM-11, ZSM-12, ZSM-23, ZSM-35, and ZSM-38, with ZSM-5 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. The free space, however, is important as the locus of catalytic activity.

Crystal framework densities of some typical zeolites including some which are not within the puriview of this invention are:

| Zeolite | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 0.5 percent by weight may be used. Thus, the original alkali metal of the zeolite may be replaced by ion exchange with cobalt, but other suitable ions of Groups IB to VIII of the Periodic Table, including, by way of example, nickel, copper, zinc, palladium, calcium or rare earth metals, also may be present.

In practicing the desired conversion process, it may be desirable to incorporate the above-described crystalline aluminosilicate zeolite in another material resistant to the temperature and other conditions employed in the process. Such matrix materials include synthetic or naturally occurring substances as well as inorganic materials such as clay, silica and/or metal oxides. The relative proportions of zeolite component and inorganic matrix on an anhydrous basis may vary widely with the zeolite content ranging from between about 1 to about 99 percent by weight and more usually in the range of about 5 to about 80 percent by weight of the dry composite.

We have found that certain matrix materials, particularly alumina, detract from the stability of the catalyst of this invention. Therefore, where a matrix or binder is used with the zeolite, it is preferred that this matrix or binder have an alumina content of less than about 10 wt. %. Silica is a preferred binder.

The particular zeolite hereinabove described is composited with sufficient cobalt to form a composition having, on an anhydrous basis, a $CoO/Al_2O_3$ molar ratio of 0.1 to about 1.0. This may be achieved by base exchange of the ammonium or hydrogen zeolite with cobalt acetate, cobalt nitrate, or other soluble cobalt salts. Compositing by impregnation also is effective. Preferred zeolites are ZSM-5, ZSM-11, ZSM-23, ZSM-35 and ZSM-38, with ZSM-5 particularly preferred.

The catalyst of this invention is required to have a minimum catalytic activity regardless of which zeolite is selected and of its cobalt content. This activity is precisely specified by determination of the "alpha value" of the catalyst, which measures its activity for the cracking of n-hexane. The alpha value is to be determined in accordance with the method set forth by P. B. Weisz and J. N. Miale in "Journal of Catalysis", Vol. 4, No. 4, August 1969, pp. 527–529, which description is herein incorporated by reference. The alpha value, for purposes of this invention, is to be at least 10, and preferably in the range of 10 to 60.

The resistance to loss of catalytic activity of the cobalt catalyst of this invention compared with other metal forms when exposed to a mixture of steam and hydrocarbons is illustrated by the drawing.

While it is not known precisely why the catalyst composition of this invention behaves in the manner it does, nonetheless, certain observations and speculations have been made which may be useful for the understanding of this invention. With perhaps the exception of the alkaline metals, such as sodium, the metal-exchanged forms of certain zeolites have been found more resistant to degradation in pure steam than the hydrogen forms of the zeolites. Thus, utilizing ZSM-5 as an example, the cobalt, copper, nickel and the zinc forms of this zeolite lose their catalytic activity when exposed to pure steam at high temperature at a slower rate than the hydrogen form. Thus, it may be speculated that cobalt and copper and other metal cations protect the alumina sites from hydrolysis.

In a steam atmosphere that contains hydrocarbons, however, copper does not appear to be effective, while cobalt is. The persistent pink color of the cobalt catalyst suggests that the cobalt ion is not reduced from its divalent metal state in the adverse environment and that its persistence in that form in a catalytic environment is needed to protect the alumina sites from degradation. On the other hand, we have noted that the copper form of the zeolite rapidly turns black in steam when hydrocarbons are present, suggesting that it is reduced from the divalent state and loses its protective function. In brief, the cationic forms of the zeolites appear to fall into two categories. In the first category are those non-reducible cations such as cobalt which retain their ionic form in a high temperature hydrocarbon-steam atmosphere, and in the second category are all the other cations, which are reduced in such an atmosphere and therefore exhibit little if any protective function.

For the purpose of this invention it is required to use a feed substantially free of sulfur, i.e. a feed that contains less than about 75 ppm of sulfur, and preferably less than 10 ppm. Any feed comprising organic compounds catalytically convertible in the presence of acid catalytic sites may be used. Typical acid catalyzed reactions of hydrocarbons contemplated as within the scope of this invention include olefin isomerization, isomerization of polyalkylbenzenes, transalkylation of aromatic hydrocarbons, paraffin isomerization, and olefin hydration. In any of these reactions, the feed is contacted under conversion conditions with the cobalt catalyst of this invention, said contacting being conducted in the presence of steam at a partial pressure of at least 0.1 atmosphere, and preferably in the range of 0.1 to about 10 atmospheres. If the feed is normally anhydrous and no water is generated in the catalytic reaction, water is added with the feed to provide said partial pressure of steam.

In general, the catalytic conversion of the process of this invention is conducted at a liquid hourly space velocity (LHSV) of from 0.5 to about 100, a temperature from about 275° C. to 600° C., and at a total pressure of from about 0.5 to 50 atmospheres.

Particularly preferred feeds are the lower aliphatic alcohols containing up to four carbon atoms, their simple or mixed ethers, or mixtures thereof. Such alcohols or ether feeds are converted to higher carbon numbered hydrocarbons with inherent formation of steam. Depending on feed and reaction conditions, the process is made to produce predominantly olefins, or olefins and aromatic hydrocarbons in the gasoline boiling range, or a liquid hydrocarbon mixture useful as high octane gasoline.

The process of this invention may be operated with a fixed stationary bed of catalyst, a fixed fluid bed, a fixed ebullated bed, or a transport bed. Accumulations of coke that may occur with detriment to the catalyst activity or selectivity may be burned off the catalyst at elevated temperature in the usual fashion. Deactivation due to long term exposure to steam is reversed by contacting the catalyst with hydrogen sulfide at a temperature about 300° to 600° C. and in an amount effective to substantially increase the alpha value of the deactivated catalyst thereby regenerating the catalyst. Hydrogen sulfide treatment may be done prior to burning to remove coke, but is most preferably done subsequent to such burning if coke-removal is required. Obvious variants of the hydrogen sulfide treatment, such as contact with thiophene, elementary sulfur, mercaptans, or, in effect any sulfur compound which will serve to convert a portion of the cobalt to cobalt sulfide, is contemplated as within the scope of this invention.

EXAMPLE 1

15 grams of an ammonium form ZSM-5 ($NH_4$-ZSM-5) having a $SiO_2/Al_2O_3$ molar ratio of about 70 to 1 was base exchanged with a solution of 29 grams of cobalt dinitrate hexahydrate in 250 ml of water to provide a cobalt-ammonium ZSM-5 containing cobalt in an amount equal to 0.89 wt. % cobalt oxide (CoO). This preparation was impregnated with an additional amount of cobalt as the dinitrate in water and dried and calcined. The final catalyst contained about 2.5 wt. % CoO, had a $CoO/Al_2O_3$ molar ratio of about 1 and considerably less than 0.5 wt. % $Na_2O$.

EXAMPLE 2

The catalyst of Example 1 was subjected to accelerated aging by contact for 120 hours at 900° F. and about 6.4 atmospheres pressure provided by about an equimolar mixture of n-hexane and steam. At the end of this cycle it had an alpha-value of about 20 determined by n-hexane cracking.

EXAMPLE 3

A portion of the aged catalyst of Example 2 was used to catalyze the conversion of methanol to hydrocarbons. After service in this conversion, it was regenerated by burning in air and contact with $H_2S$ at 950° F. Regeneration doubled the catalytic activity for methanol conversion.

What is claimed is:

1. In a process for manufacturing hydrocarbons from a feed comprising one or more compounds selected from the group consisting of the lower monohydric alcohols with up to four carbon atoms and their simple and mixed ether derivatives, said process comprising passing said feed at a space velocity of about 0.5 to about 100 L.H.S.V. over a catalyst contained in a reaction zone, said catalyst comprising a crystalline alumino-silicate zeolite having a Constraint Index of 1.0 to 12.0 and a silica to alumina ratio of at least about 12, with the temperature in said reaction zone at about 275° C. (507° F.) to about 600° C. (1112° F.), and withdrawing from said reaction zone an effluent comprising steam and hydrocarbons, said process being characterized by a progressive catalyst deactivation due to the high temperature exposure to said steam; the improvement, whereby extending catalyst life, which comprises in combination:

utilizing as catalyst said crystalline aluminosilicate zeolite composited with 0.1 to about 1.0 mol of cobalt oxide per mol of zeolitic alumina; and reactivating said catalyst after steam deactivation, said reactivation being effected by contact with hydrogen sulfide.

2. The process described in claim 1 wherein the catalyst is substantially free of alkaline metal.

3. The process described in claim 1 wherein the catalyst is substantially free of alkaline metal and is characterized by an alpha value of at least 10.

4. The process described in claim 1 wherein the feed is methanol, dimethylether, or a mixture thereof.

5. The process described in claim 2 wherein the feed is methanol, dimethylether, or a mixture thereof.

6. The process described in claim 3 wherein the feed is methanol, dimethylether, or a mixture thereof.

7. The process described in claim 4, or 5 or 6 including the step of recovering an olefin from said withdrawn hydrocarbon.

8. The process described in claim 4 or 5 or 6 including the step of recovering an aromatic hydrocarbon compound from said withdrawn hydrocarbon.

* * * * *